(12) United States Patent
Bain

(10) Patent No.: US 12,364,645 B2
(45) Date of Patent: Jul. 22, 2025

(54) ENHANCED PROPHYLACTICS FOR VACUUM THERAPY

(71) Applicant: Growth Armor, LLC, Wilmington, DE (US)

(72) Inventor: Michael A. Bain, Costa Mesa, CA (US)

(73) Assignee: Growth Armor, LLC, Wilmington, DE (US)

( * ) Notice: Subject to any disclaimer, the term of this patent is extended or adjusted under 35 U.S.C. 154(b) by 876 days.

(21) Appl. No.: 17/646,309

(22) Filed: Dec. 29, 2021

(65) Prior Publication Data
US 2023/0201071 A1    Jun. 29, 2023

(51) Int. Cl.
| A61H 19/00 | (2006.01) |
| A61F 6/04 | (2006.01) |
| A61H 9/00 | (2006.01) |

(52) U.S. Cl.
CPC .............. *A61H 19/32* (2013.01); *A61F 6/04* (2013.01); *A61H 9/0057* (2013.01); *A61H 2201/1238* (2013.01); *A61H 2201/1409* (2013.01); *A61H 2201/1645* (2013.01); *A61H 2201/165* (2013.01)

(58) Field of Classification Search
CPC .......... A61F 6/04; A61F 2006/041–049; A61F 5/41; A61F 2005/411–418; A61H 19/32; A61H 19/50
See application file for complete search history.

(56) References Cited

U.S. PATENT DOCUMENTS

| 4,671,262 A | 6/1987 | West | |
| 4,690,135 A * | 9/1987 | Gerow | A61F 5/41 600/39 |
| 4,984,582 A * | 1/1991 | Romaniszyn | A61F 6/00 604/349 |
| 5,050,619 A | 9/1991 | Ferguson | |

(Continued)

FOREIGN PATENT DOCUMENTS

| CN | 111821093 A | 10/2020 |
| FR | 2772260 A1 | 6/1999 |

OTHER PUBLICATIONS

PCT Search Report and Written Opinion for PCT/US 22/52693; Mar. 28, 2023.

*Primary Examiner* — Thaddeus B Cox
(74) *Attorney, Agent, or Firm* — Stetina Garred Brucker & Newboles

(57) ABSTRACT

An improved condom-style vacuum therapy device has a region of the sheath formed of an air-permeable material that is covered by an air-impermeable barrier so as to define a lumen therebetween. A conduit defining an airflow pathway is located in fluid communication with the lumen, and is connected to a vacuum source in order to draw air out of the interior of the condom-style device through the air-permeable region. When the condom-style device is worn over the penis, a sealing element proximate to the open end serves to at least partially restrict the intrusion of ambient air into the condom. As a result, the air pressure within the sheath of the condom is reduced to below ambient air pressure, serving to prevent or treat actual or potential erectile dysfunction and/or to enhance sexual performance, while also providing the prophylactic and/or contraceptive benefits associated with condom use.

15 Claims, 2 Drawing Sheets

(56) References Cited

U.S. PATENT DOCUMENTS

| | | | |
|---|---|---|---|
| 5,377,692 A | 1/1995 | Pfeil | |
| 6,458,073 B1* | 10/2002 | Bonthuys | A61F 5/41 600/38 |
| 8,622,889 B1* | 1/2014 | Loria | A61F 5/41 600/38 |
| 2006/0229494 A1* | 10/2006 | Wu | A61F 5/41 600/38 |
| 2007/0017528 A1* | 1/2007 | Osterberg | A61H 23/02 128/844 |
| 2011/0040142 A1* | 2/2011 | Eum | A61F 5/41 600/38 |

* cited by examiner

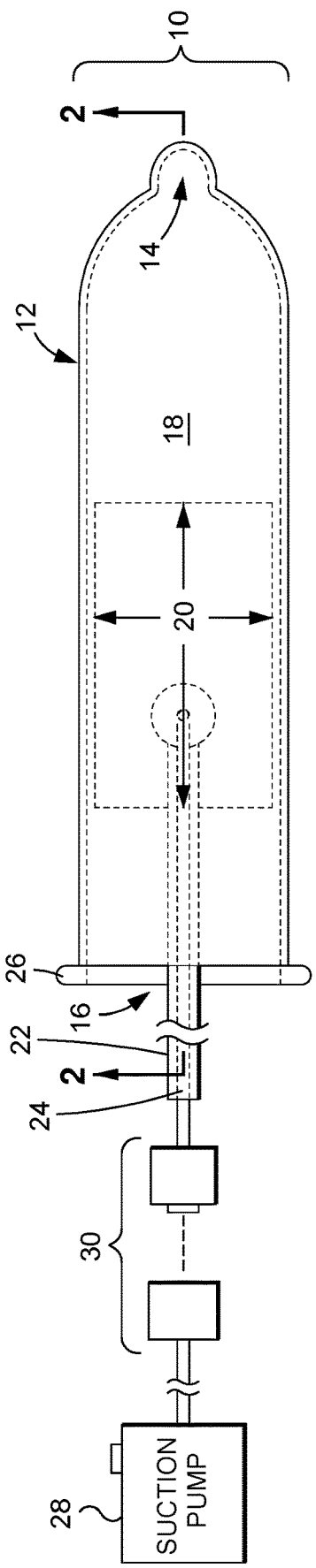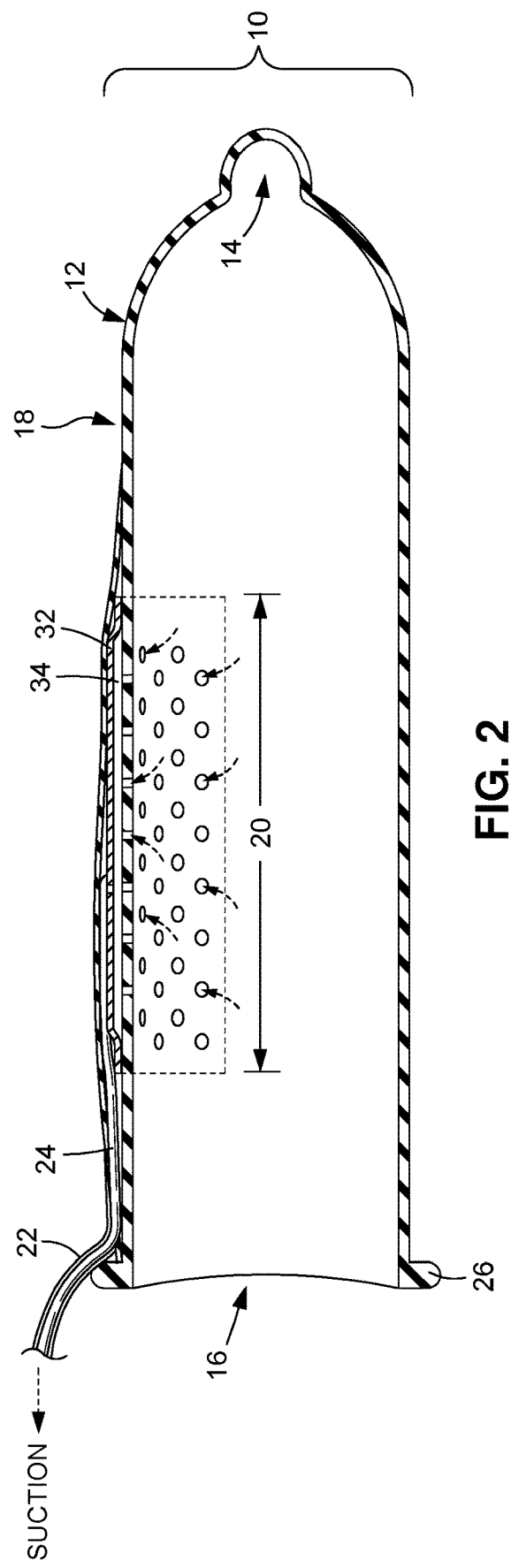

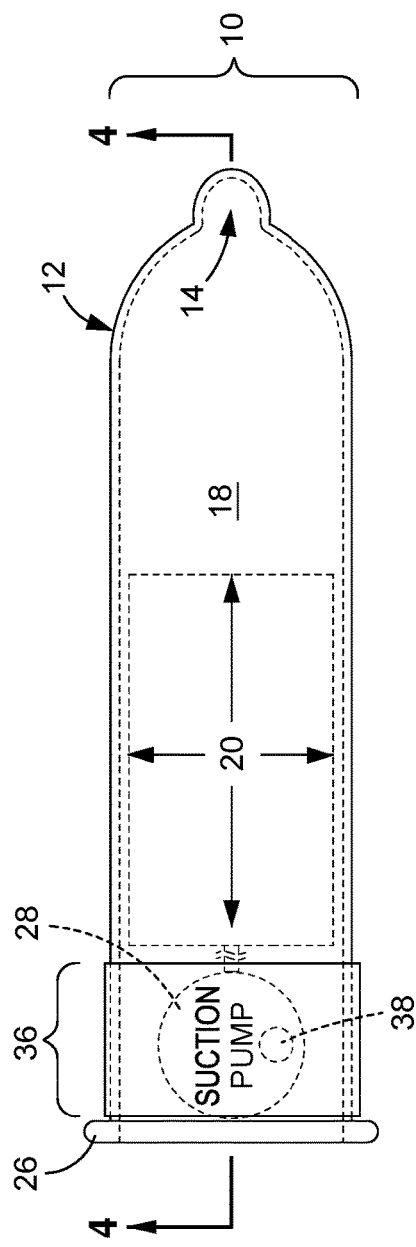
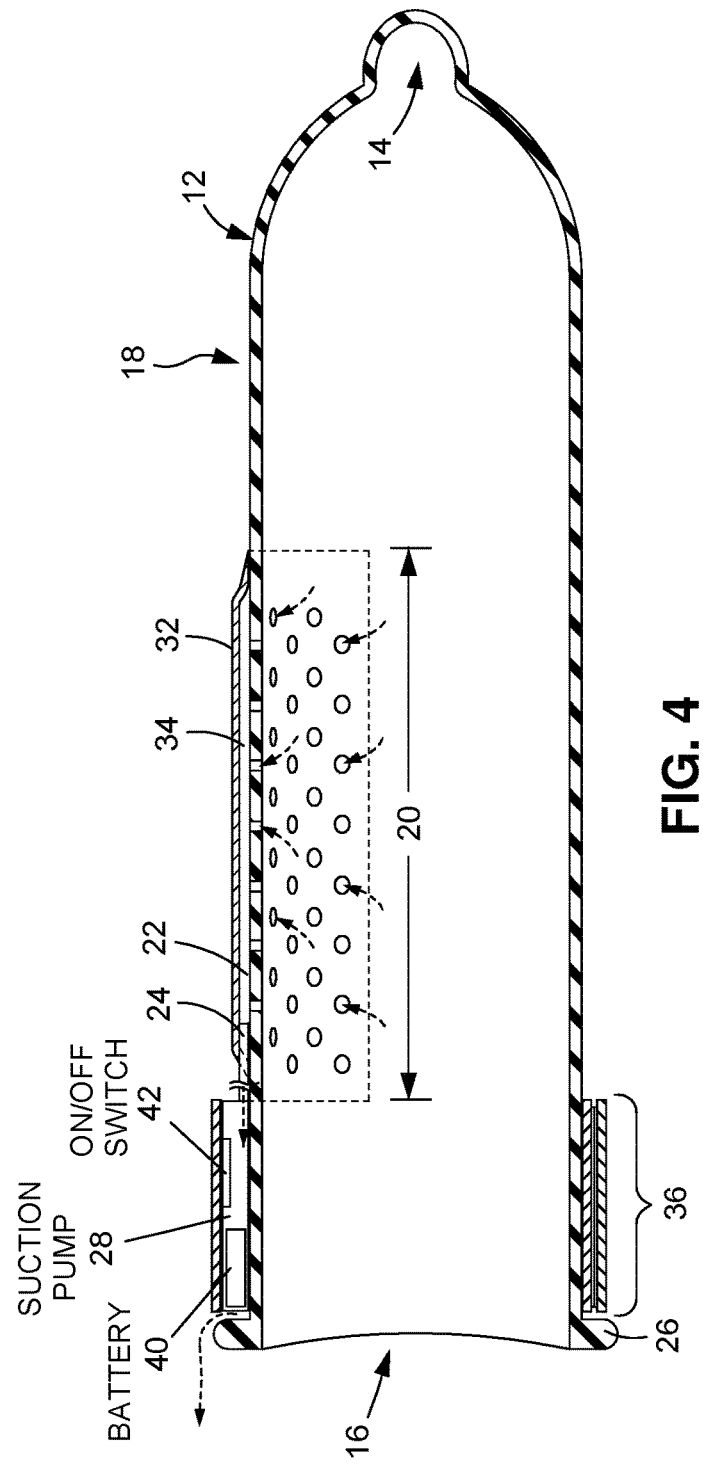
FIG. 3
FIG. 4

ENHANCED PROPHYLACTICS FOR VACUUM THERAPY

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the fields of prophylaxis and contraception, and the treatment of erectile dysfunction. More particularly, the present disclosure relates to superior devices and methods which are effective in treating or preventing erectile dysfunction and/or enhancing sexual stimulation while also providing similar prophylactic and contraceptive effects as in conventional condom-style prophylactic devices.

2. Related Art

The number of U.S. men with erectile dysfunction has been estimated to be between 10 to 20 million, and inclusion of individuals with partial erectile dysfunction increases this estimate to over 30 million. The male erectile response is initiated by the action of neurons, or nerve cells (i.e., neuronal action), and maintained by a complex interplay between events involving blood vessels (i.e., vascular events) and events involving the nervous system (i.e., neurological events).

The part of the nervous system that regulates involuntary action (e.g., the intestines or the heart) is called the autonomic nervous system. The autonomic nervous system is divided into two mutually antagonistic systems: the sympathetic nervous system and the parasympathetic nervous system. The sympathetic nervous system originates in the thoracic and lumbar regions of the spinal cord, and in general, opposes the physiological effects of the parasympathetic nervous system. For instance, the sympathetic nervous system will tend to reduce digestive secretions or speed up the heart, usually when an individual is in an active state. The parasympathetic nervous system originates in the brain stem and the lower part of the spinal cord, and, in general, opposes the physiological effects of the sympathetic nervous system. Thus, the parasympathetic nervous system will tend to stimulate digestive secretions or slow the heart usually when an individual is in a relaxed state.

The male erectile response is initiated by of parasympathetic neuronal action. Specifically, this parasympathetic input originates at the pelvic splanchnic nerve plexus. The pelvic splanchnic nerve plexus is comprised of branches from the second, third, and fourth sacral nerves (from the lower part of the spinal cord) that intertwine with the inferior hypogastric plexus, which is a network of nerves in the pelvis. The cavernous nerves are derived from the pelvic splanchnic nerve and supply parasympathetic fibers to the corpora cavernosa and corpus spongiosum, the erectile tissue in the penis containing large interspaces capable of being distended with blood.

This activity allows erection by relaxation of smooth muscle (i.e., muscle that contract without voluntary control) and dilation of the helicine arteries, which are coiled arteries found in the erectile tissue of the penis. The dilation of the arteries causes greatly increased blood flow through the erectile tissue, which leads to expansion of the three cylinders of erectile tissue in the penis (i.e., the corpora cavernosa and the corpus spongiosum). As the corpora cavernosa and the corpus spongiosum expand, the venous structures draining the penis are compressed against the fascia surrounding each of the erectile tissues (i.e., the tunica albuginea of the corpora cavernosa and the tunica albuginea of the corpus spongiosum). Thus, the outflow of blood is restricted, and the internal pressure increases. This vein-obstruction process is referred to as the corporal veno-occlusive mechanism.

Erectile dysfunction may be the result of any number of causes, both physiological and psychological, and in many patients the disorder may be caused by multiple factors. The causes may include several that are essentially neurologic in origin. Damage to the pathways used by the autonomic nervous system to innervate the penis may interrupt erection initiated by the central nervous system. Lesions of the somatic nervous pathways (the nerves associated with sensation or motion), which may be caused by injury, infection, or disease, may also impair, and may interrupt tactile sensation needed to maintain psychogenic erections. Spinal cord lesions may also produce varying degrees of erectile failure depending on the location and severity of the lesions.

Disorders leading to peripheral neuropathy may also impair neuronal innervation of the penis. Peripheral neuropathy is an abnormality of the part of the nervous system constituting the nerves outside the central nervous system, which include the cranial nerves, the spinal nerves, and the sympathetic and parasympathetic nervous systems. Peripheral neuropathy may also impair neuronal innervation of the sensory afferents—the nerves that conduct impulses from the periphery of the body to the brain or spinal cord. Peripheral neuropathy is a potential result of a number of diseases, such as diabetes mellitus.

The endocrine system, particularly the production of androgens (steroid hormones, such as testosterone or androsterone, that control the development and maintenance of masculine characteristics), also appear to play a role in regulating sexual interest and may also play a role in erectile function. As men age, their production of androgens typically decreases.

In men of all ages, erectile failure may diminish willingness to initiate sexual relationships because of fear of inadequate sexual performance or rejection. Because men, especially older men, are particularly sensitive to the social support of intimate relationships, withdrawal from these relationships because of such fears may have a negative effect on their overall health.

Some forms of erectile dysfunction are treated with medication, with varying degrees of success. For instance, the oral medication sildenafil citrate requires an hour to exert its full effects, and it may have significant side effects such as abnormal vision, flushing, headache, and diarrhea.

Invasive or surgical treatments are also known to be used to treat erectile dysfunction. Intracavernosal injection therapy is a potential way of treating erectile disfunction in which a patient injects vasodilator substances (e.g., alprostadil, papaverine, phentolamine) into the corpora of the penis. Electrical stimulation implants have also been used, but require significant surgical procedures for placement of electrodes, leads, and processing units. These devices may also require an external apparatus that needs to be strapped or otherwise affixed to the skin. However, due to the requirement for injection or surgery, these treatments are not preferred by patents.

Therapeutic application of vacuum devices is also a way in which erectile dysfunction has been treated in the past. Penis pumps, which cause or enhance an erection of a penis, have been known in the art for some years. The manner in which such pumps work is by placing a chamber over a flaccid penis and evacuating the chamber. The evacuation causes a pressure differential between the inside and outside of the chamber. The lower pressure within the chamber causes blood to flow into the penis and thus make the penis erect.

Vacuum devices are at times effective at generating and maintaining erections in some patients with erectile dysfunction. However, as with injection therapy, there is significant patient dissatisfaction with such devices: the devices are difficult for many patients to use, are bulky, and are generally difficult to use. Further complicating their use, partner involvement and training with vacuum/constriction devices is often important for successful outcome, especially in regard to establishing a mutually satisfying level of sexual activity. In situations in which sexual activity may be desired to be more spontaneous, the use of overt and bulky vacuum/ constriction devices will likely be disfavored, due to the perception that such use will be likely to result in dissatisfaction or embarrassment, especially with a sexual partner who may not be aware of the user's medical condition.

In contrast, the use condoms for prophylactic and/or contraceptive purposes is generally considered to be accepted even in the most spontaneous sexual encounters for all men, regardless of whether or not they suffer from erectile disfunction. Condoms have a small form factor, and do not generally require significant training to use. Further does discovery of a condom-style product immediately inform that the owner suffers from erectile disfunction, in the way discovery of a large conventional vacuum device would be likely to.

It is therefore desirable to have improved devices and methods for providing vacuum therapy device in the form factor of a condom, which also serves to accomplish the prophylactic and contraceptive functions of a condom.

BRIEF DESCRIPTION

To solve these and other problems, an improved condom-style prophylactic device is contemplated in which a region of the sheath of the condom-style device is formed of an air-permeable material and is covered by an air-impermeable barrier so as to define a lumen therebetween. A conduit with an airflow pathway is located in fluid communication with the lumen, and is connected to a vacuum source in order to draw air out of the interior of the condom-style device. When the condom-style device is worn over the penis, a sealing element proximate to the open end serves to at least partially restrict the intrusion of ambient air into the condom. As a result, the air pressure within the sheath of the condom is reduced to below ambient air pressure, serving to prevent or treat actual or potential erectile disfunction and/or to enhance sexual performance, while also providing the prophylactic and/or contraceptive benefits associated with condom use.

According to one exemplary embodiment of the present disclosure, an enhanced prophylactic device is contemplated, the enhanced prophylactic device comprising a sheath comprising an elastic tubular membrane having a closed distal end, an open proximal end, and an external side, the elastic tubular membrane having an air permeable region, a barrier positioned over an area of the external side of the elastic tubular membrane encompassing at least the air permeable region, the barrier and the area of the external side of the elastic tubular membrane over which the barrier is positioned defining a lumen region therebetween, a conduit defining an airflow pathway in fluid communication with the lumen region; and a sealing element proximate to the open proximal end, the sealing element being adapted to at least partially restrict the intrusion of ambient air into the open proximal end when the enhanced prophylactic device is worn over the penis of a wearer, wherein when the sheath is worn over the penis of a wearer and the airflow pathway of the conduit is placed in fluid communication with a vacuum source, the enhanced prophylactic device is operative to reduce air pressure within the sheath to below ambient.

It is further contemplated that the enhanced prophylactic device may incorporate a vacuum source in fluid communication with the airflow pathway. According to certain particular embodiments, the vacuum source may comprise a suction pump, which may be electronically powered.

According to more particular embodiments of the herein contemplated devices, the suction pump may be contained within a pump housing element. The pump housing element may be adapted to be worn by the wearer of the enhanced prophylactic device. For example, the pump housing element may be adapted for annular engagement so as to be worn around a portion of the penis. According to various embodiments, the pump housing element may be configured to be worn around a portion of the penis not enclosed by the sheath, or to be worn around a portion of the penis at least partially enclosed by the sheath, either over or underneath at least a portion of the sheath.

In addition, or alternatively to any of these embodiments, the pump housing element may be constructed in a fashion such that it is integral with the sheath. The pump housing element may also be construction in a fashion such that it is integral with and/or serves as the sealing element.

It is also contemplated that the pump housing element may further comprise a stimulatory module adapted to intensify sexual stimulation of the wearer or a sexual partner of the wearer. According to certain more particular embodiments, the stimulatory module may comprise a vibrational element.

It is further contemplated that the pump housing element may further comprise a power source for operating at least the suction pump. The power source may, for example, comprise a battery. The pump housing element may also further comprise a control module for permitting the wearer to control the suction pump, which may be, for example, a toggle switch.

Also contemplated are methods for treating sexual dysfunction using certain of the herein contemplated devices. For example, an exemplary method may comprising the steps of: (1) providing an enhanced prophylactic device, the enhanced prophylactic device comprising a sheath comprising an elastic tubular membrane having a closed distal end, an open proximal end, and an external side, the elastic tubular membrane having an air permeable region a barrier positioned over an area of the external side of the elastic tubular membrane encompassing at least the air permeable region, the barrier and the area of the external side of the elastic tubular membrane over which the barrier is positioned defining a lumen region therebetween a conduit defining an airflow pathway in fluid communication with the lumen region, and a sealing element proximate to the open proximal end, the sealing element adapted to at least partially restrict the intrusion of ambient air into the open proximal end when the enhanced prophylactic device is worn over the penis of a wearer; (2) positioning the sheath over the penis of the wearer; and (3) placing the airflow pathway of the conduit in fluid communication with a vacuum source so as to reduce air pressure within the sheath to below ambient.

The present disclosure will be best understood by reference to the following detailed description when read in conjunction with the accompanying drawings.

BRIEF DESCRIPTION OF THE DRAWINGS

These and other features and advantages of the various embodiments disclosed herein are better understood with respect to the following descriptions and drawings, in which:

FIG. 1 is a top cutaway view illustrating an enhanced prophylactic device according to one exemplary embodiment of the present disclosure in which the vacuum source is configured to be independently located from the sheath;

FIG. 2 is a side cross-sectional view illustrating in more detail the exemplary embodiment of the enhanced prophylactic device shown in FIG. 1.

FIG. 3 is a top cutaway view of an enhanced prophylactic device according to another exemplary embodiment of the present disclosure in which a pump housing element is configured to be worn fastened over the sheath; and FIG. 4 is a side cross-sectional view illustrating in more detail the exemplary embodiment of the enhanced prophylactic device shown in FIG. 1.

Common reference numerals are used throughout the drawings and the detailed description to indicate the same elements.

DETAILED DESCRIPTION

According to the various examples discussed herein, improved vacuum devices for treating erectile disfunction and methods of using such devices are contemplated in which a region of the sheath of a condom-style device may be formed of an air-permeable material and is covered by an air-impermeable barrier so as to define a lumen therebetween. A conduit with an airflow pathway may be located in fluid communication with the lumen, and may be connected to a vacuum source in order to draw air out of the interior of the condom-style device. When the condom-style vacuum device is worn over the penis, a sealing element proximate to the open end may serve to at least partially restrict the intrusion of ambient air into the condom. As a result, the air pressure within the sheath of the condom is reduced to below ambient air pressure, serving to prevent or treat actual or potential erectile disfunction and/or to enhance sexual performance, while also providing the prophylactic and/or contraceptive benefits associated with condom use.

Turning now to FIG. 1, a top view of an exemplary embodiment of an enhanced prophylactic device 10 according to the present disclosure is shown. As may be seen, the enhanced prophylactic device 10 may include a sheath 12 with a closed distal end 14, an open proximal end 16, an external side 18, and an air permeable region 20. The enhanced prophylactic device 10 may also include a conduit 22 defining an airflow pathway 24, which may be connectible to a vacuum source 28 via a valve 30. The enhanced prophylactic device 10 may also include a sealing element 26 which may be positioned proximate to the open proximal end.

The sheath 12 may be generally formed of any material for which a conventional prophylactic and/or contraceptive condom may be formed, including but not limited to latex, polyisoprene, and polyurethane. It should be recognized, however, that the general purpose of a condom is to serve as a barrier to the passage of bodily fluids, and that any material may be utilized which at least partially accomplish this purpose. While it may be preferable for the sheath 12 in many or most embodiments of the present disclosure to be substantially impermeable to air, it may not be entirely necessary for the majority of the material of the sheath 12 to necessarily be completely impermeable to the passage of air. The sheath may also be of size or shape considered suitable for use in the fashion of a conventional prophylactic/contraceptive condom, as long as it has a closed distal end 14 and an open proximal end 16.

The sheath may have an air permeable region 20. It should be recognized that the term air permeable is a matter of relative degree. Some materials, including materials in the form in which they are conventionally used for contraceptive and prophylactic barriers such as latex rubber, are generally considered to be impermeable to the passage of air in general usage, owing to having extremely low air and sometimes nearly undetectable levels of permeability on the molecular level are generally considered to be air impermeable. However, it may be seen that even materials such as latex rubber, polyisoprene, polyurethane that are, in conventional usage in condom products, generally considered to be air impermeable, may be manufactured or formulated in ways in which they may be substantially more permeable to the passage of air. As such, the term "air permeable" as used herein should be viewed as relative term which indicates that the air permeable region 20 has a higher level of air permeability than the material(s) that generally form the other areas of the sheath 12. Many types of air permeable regions 20 may conceivably be utilized in the embodiments of the present disclosure, without departing from its scope and spirit. For example, it may be that the air permeable region 20 simply consists of a one or more apertures within the sheath 12, for example, an array of many small apertures, positioned at a region of the sheath 12 which otherwise is formed of the same type and quality of materials as the remainder of the sheath outside of the air permeable region 20. It may be seen that this approach may have certain advantages, for example, in ease of manufacture and in structural integrity. However, according to other embodiments, it is contemplated that the air permeable region 20 may be formed of a different type or quality of materials than the materials of remainder of the sheath 12 outside of the air permeable region 20. For example, it is contemplated that the air permeable region 20 may be ideally formed a material such as a "breathable" or a vapor permeable membrane which is generally amenable to the passage across the membrane of air molecules, but resistant to the passage of water molecules and other liquids (for example, bodily fluid), and such materials are well-known and characterized for use in the field of medical devices and prosthetics. One example of a suitable vapor permeable membrane may be expanded polytetrafluoroethylene (ePTFE), which is used in many breathable membranes manufactured by manufacturers such as W.E. Gore and Associates for use in medical and consumer products. However, it may be seen that a breathable membrane may be only one example of a material which may be used in an air permeable region 20 of the sheath 12 according to the present disclosure, and indeed, many other materials and/or structures may be utilized to achieve such an air permeable region 20, as long as a greater volume of airflow is enabled to transit across the air permeable region 20 compared to the remainder of the sheath 12, such that when suction is applied to the air permeable region, the air pressure within the sheath may be reduced to a level below ambient.

The sealing element 26 may be any structure or component thereof which is adapted to function so as to at least partially restrict the intrusion of ambient air into the open proximal end 16 of the sheath 12 when the sheath 12 is worn over the penis of the wearer. In the embodiment illustrated in FIG. 1, the sealing element 26 comprises a rim on the base of the sheath at the open proximal end 16 which may be seen to exert a more substantial force of elasticity than the remainder of the material of the sheath 12 owing to its greater thickness. However, in other embodiments, it may be seen that the sealing element 26 may be other structures or components of structures, which may or may not be subsidiary components of the sheath 12 or of other components of the enhanced prophylactic device 10. For example, it may be seen that the sealing element may, in other embodiments, be an entirely separate structure that attaches over or under the sheath 12 proximate to the open proximal end 16. Many types of structures or components of structures are envisioned as capable of being adapted to perform the function of the sealing element 16, including bands, straps, tensioners, etc., and it may be seen that the exact identity of the structure which performs the function of the sealing element 16 may not necessarily be critical to the scope and spirit of the present disclosure, as long as its function of at least partially restriction the intrusion of ambient air into the open proximal end 16 of the sheath 12 when the sheath 12 is worn over the penis of the wearer is achieved. It may thus be further seen that the structure which performs this function may also serve a further purpose in addition, such as serving as an attachment or mounting point for another component, such as a strap which also maintains a suction device in a proper position in relation to the sheath 12.

The vacuum source 28 may be any vacuum source which may be operative to, when placed in fluid communication with the air permeable region 20 of the sheath 12 when it is worn over the penis of the wearer with the sealing element 26 at least partially restricting the intrusion of ambient air into the open proximal end 16 of the sheath 12, to reduce the air pressure within the sheath 12 to below ambient. It may thus be seen that in the exemplary embodiment, the vacuum source 28 may be a suction pump, and specifically an electronically powered suction pump. However, it may be seen that any vacuum source 28 may be utilized to accomplish the purpose of the present disclosure, including, for example but without limitation, suctions pumps which are powered other than via electronic power, such as via mechanical power, such as in hand pumps which may be actuated by the wearer or a wearer's sexual partner. It may also be seen that the vacuum source 26 may not necessarily be a suction pump at all, but instead may simply be a vacuum reservoir. Many types of vacuum sources 26 are conceivable as being within the scope and spirit of the present disclosure, and the exact identity of the vacuum source may not, in some conceptions of the presently described disclosure, be necessarily critical, and it should be seen that many alternative vacuum sources 26 may be used according to the herein described systems and methods of operation.

Further, it may be seen that the vacuum source 28 may be entirely distinct from the remaining elements of the device, such as a generic suction pump, or may be configured especially for use with the remainder of the device. For example, it may be seen that a suction pump may be attached to the wearer, such as via belt or strap. According to one particular embodiment, it should be appreciated that a suction pump may be attached to a strap, clip, or elastic band, and may be secured around the sheath 12 proximate to the open proximate end 16, with the strap, clip, or elastic band further being adapted to function as the sealing element 28. Alternatively, the attachment to the penis may simply be a form of attachment alone, such as a strap which may secure the vacuum source to the wearer's penis over or under the sheath, or at a region of the wearer's penis which the sheath 12 does not cover. The exact location at which the vacuum source 28 may be located and/or retained in place may not be critical to the functionality of any particular embodiment of the present disclosure, as long as that the vacuum source 28 operates in conjunction with the other components of the device to reduce the air pressure within the sheath to below ambient.

A conduit 22 defining an airflow pathway 24 may be utilized to place the vacuum source 28 in fluid communication with the air permeable region 20 so as to enable the reduction in air pressure within the sheath 12 to below ambient. Optionally, the conduit 24, and optionally the vacuum source 28, may also include one or more valve elements 30 as well, in order to enable interconnectivity between different sections of conduit 22 or between the conduit 22 and the vacuum source 28. In the exemplary embodiment, the conduit 22 is a section of tubing formed of a silicone polymer or a polysiloxane. However, it may also be seen that a suitable tubing may be formed of another polymer material such as polyvinyl chloride, polyethylene, nylon, a thermoplastic elastomer, or any other material known in the art to be useful and suitable for forming sections of tubing. It should be appreciated that the exact identity of the material used to form the conduit 22 which defines the airflow pathway 24 may not necessarily be critical to the scope and spirit of the present disclosure, as long as its function of defining the airflow pathway 24 so as to place the vacuum source 28 in fluid communication with the air permeable region 20 so as to enable the reduction in air pressure within the sheath 12 to below ambient. Further, it should be appreciated that the presence or absence, or the number or identity or structure of any valves or interconnection devices in the pathway between the vacuum source 28 and the air permeable region 20 is not necessarily critical, and that the presence of valves or interconnection devices at any location is permissible, including valves or interconnection devices which interconnect via different methods, such as frictional engagement, threaded engagement, etc. Such valves may be simple interconnection devices, or may be one-way valves designed to allow for the flow of air in only a single direction, which may be useful in order so that the a vacuum source need not be continually connected to the remainder of the device.

Turning now to FIG. 2, a more detailed cross-sectional side view of an exemplary embodiment of an enhanced prophylactic device 10 is shown. It may be seen that according to the exemplary embodiment illustrated, a barrier 32 may be positioned over an area of the external side 18 of the sheath 12 which encompasses at least the air permeable region 20, in order to define a lumen region 34 between the barrier 32 and the area of the external side 18 of the sheath over which the barrier 32 is positioned. It may therefore be seen that the airflow pathway 24 of the conduit 22 may be placed in fluid communication with the lumen region 34 so as to affect the application of vacuum from the vacuum source 28 to the air permeable region 20 in order to reduce the air pressure within the sheath 12 to below ambient. It may be preferable, in some embodiments, for the barrier 32 to be substantially impermeable to the passage of air, so as to both result in a greater effect of the application of the vacuum source to the air permeable region without losses in suction due to intrusion of ambient air into the airflow pathway 24 or the lumen region 34, as well as to prevent the passage of any liquids (such as bodily fluids) into the lumen region 34, and thereafter potentially into the interior of the sheath 12, which may potentially occur if the air permeable region is not itself sufficiently impermeable to such liquids. It may also be preferable for barrier 32 to be substantially integral with the external surface 18 of the sheath 12 at the location at which a junction therebetween occurs, or at least to have as little discontinuity as possible at the junction therebetween, in order to prevent any potential discomfort or displacement or tearing of the barrier from occurring during sexual activity while wearing the enhanced prophylactic device 10. With regard to the conduit 22, it may be seen that the conduit 22 may be interfaced with the barrier 32 so as to place the airflow pathway 24 defined by the conduit 22 in fluid communication with the lumen region 34, and that such interfacing may occur in any number of ways, including, for example but without limitation, having the conduit 22 terminate at or extend at least partially into the lumen region 34, either through the barrier 32 or the sheath 12, or through a junction therebetween, or via the use of one or more valves 30 to connect the conduit to the barrier 32 or the sheath 12, or at the junction therebetween. Other methods of interfacing the conduit 22 with the barrier 32 so as to place the airflow pathway 24 in fluid communication with the lumen region 34 may be readily conceived, and thus should not be excluded from the scope and spirit of the present disclosure.

Turning now to FIG. 3, an embodiment of an enhanced prophylactic device 10 is shown in which the vacuum source 28 is a suction pump which is contained within a pump housing element 36. As may be seen in the illustrated embodiment, the pump housing element 36 need not be located entirely distant from the sheath 12, as the vacuum source 28 is shown in FIG. 1, but instead may be annularly attached around and over a portion of the sheath 12. In this fashion, it may be seen that the form factor of the enhanced prophylactic device 10 may be substantially reduced, such that it may be possible for the enhanced prophylactic device 10 to be nearly visually indistinct from a conventional condom, such that a wearer's sexual partner may not even be necessarily aware that the wearer is utilizing a vacuum therapy device. The pump housing element 36 may optionally even be made to be highly integrated with the sheath 12, and potentially may be included as a part of the sheath 12, such as for example, being integrally included within the material of the sheath so as to be visually concealed. In this fashion, the pump housing element 36 may be discarded along with the sheath 12 after use. However, it may alternatively be preferable for the sheath 12 to be a consumable component that may be discarded and replaced after each use, while the pump housing element 36 may be an enduring reusable component which may be repeatedly utilized with multiple sheaths 12.

A user may utilize an enduring reusable pump housing 36 by, for example, securing it in it around the sheath 12 before or after placing the sheath 12 over the wearer's penis, and thereafter connecting the conduit 24 to a suitable attachment point on or projecting from the pump housing 36, so as to establish fluid communication between the suction pump and the lumen region 34. When the suction pump is thereafter activated with the sheath 12 worn over the penis and the sealing element 26 serving to at least partially restrict the intrusion of ambient air into the open proximal end 16, the air pressure within the sheath may thus be reduced to below ambient. Further, it may also be seen that the attachment mechanism of the pump housing element 36 to the sheath 12 may further serve to function as the sealing element 26, for example, via a strap or elastic band interconnecting the pump housing element 36 to the sheath 12 or via the structure of the pump housing 36 itself being correctly sized or adjustable in size or configuration so as to fit around the sheath in a manner sufficiently snug to provide the necessarily seal. Following use, the user may then disconnect the pump housing element 36 from the sheath, and discard the sheath 12 while retaining the pump housing element 36 for subsequent use.

It is further contemplated that the pump housing element 36 may include further components in addition to a vacuum source 28. According to one exemplary embodiment, it is contemplated that the pump housing element 36 may also include a stimulatory module adapted to intensify sexual stimulation of the wearer or a sexual partner of a wearer. For example, the stimulatory module may be, without limitation, a vibrational element sized and configured to deliver vibrations at a frequency adapted to provide sexual stimulation. The use and functionality of vibrational elements or other stimulatory modules to provide sexual stimulation is generally well known in the art, and need not be detailed here. Further, it is contemplated that any known or future developed stimulator module may be included or incorporated with a pump housing element 36 as herein described and still remain within the scope and sprit of the present disclosure. For example, other stimulatory modules in addition to vibrational elements may include, without limitation, electrical stimulation elements, movable elements, fluid manipulation elements such as blowers, jets, bladders, or dispensers adapted to project or release a fluid such as a liquid or gas (for example, a stream of air, an aerosol, or a lubricant), or particular configurations or contours of the pump housing element 36 adapted to contact or otherwise apply pressure to particular anatomical regions of the wearer and/or a wearer's sexual partner.

Turning now to FIG. 4, a side cross-sectional view of an enhanced prophylactic device 10 according to the present disclosure is shown, in which an interior of one particular embodiment of a pump housing element 36 is shown. In accordance with this illustration, it may be seen that this particular embodiment of a pump housing element 36 may include, in addition to the vacuum source 28, a power source 40 for operating at least the suction pump, and a control module 42 for permitting the wearer to control the functionality of the components of the pump housing element 36, including at least the suction pump.

The power source 40 is, in the exemplary embodiment, a battery, which may be seen to, in addition to powering the suction pump, power any other electronically powered devices as well. However, it may also be appreciated that the power source 40 may be another power source other than a battery, such as a receptable or connection point for an electronic power cord for receiving electrical power from a remote source, or a source of mechanical power such as a spring under tension, a compressed air reservoir, a hand-powered device for actuating the suction pump, etc. It may further be seen that in the case of the power source 40 being a battery, it may be a rechargeable battery which may not be intended to be generally removed form within the pump housing element 36, but rather recharged periodically via any potential methods of recharging batteries known in the art, or the battery may be a consumable battery which is intended to be discarded and replaced when appropriate, via any sort of method of accessing the consumable battery known in the art. Further, it may be seen that the power source 40 may be used to power, in addition to the suction pump, such further components as which may be included within the pump housing element 36 as may require or benefit from power to function, such as any of the above-described stimulatory modules like a vibrational element. It may further be seen that the pump housing element 36 may contain a single power source 40 or group of power sources 40 for collectively powering each element within which may utilize power, or may contain multiple distinct power sources 40 which each individually power a single element. It may thus further be seen that configuration of the different elements within the pump housing element 36 may be adapted to be permanently joined within the pump housing element 36, or may be various reconfigurable, including attachable or removable, from the pump housing element 36, such as in the case of a vibrational element, where the user may desire to include or not include the vibrational element during use, and as such may reconfigure the pump housing element 36 so that the vibrational element is no longer attached or no longer serves to provide sexual stimulation to the wearer and/or a wearer's sexual partner, or is reconfigured or reposition to provide sexual stimulation in a different fashion or to a different person. Likewise, a user may swap one sexual stimulation element for another, such as by removing a vibrational element in favor of an electrical stimulation element.

In the exemplary embodiment, the control module 42 comprises a simple toggle switch for actuating the suction pump in a simple on/off arrangement, and the configuration and use of such toggle switches are readily known in the art. However, it may be seen that the control module 42 may be any sort of control module for permitting a user to control the functionality of the suction pump or any of the other optional elements within the pump housing element 36, such as buttons, touchscreens, or other methods of controlling a physical device. In particular, it is contemplated that methods of wired or wireless transmission of signals to a remote controller may be utilized. For example, it is contemplated that the control module 42 may comprise a wireless transmitter and/or receiver, such as a Bluetooth or Wi-Fi transponder which may be used in conjunction with a controller such as a user's smartphone, which may optionally have software installed on it to permit a user to control the suction pump and/or other optional elements within the pump housing element 36. In this fashion, the control module may reside partially within the pump housing element 36, and partially within another device of the user, such as a remote control, a smartphone, a laptop computer, etc., and the control features may be substantially more customized, especially given the available room on a pump housing element such as the one shown in the illustration of FIG. 4. For example, it may be desired for the user to specifically control the strength of the suction pump or to define a pressure at which the suction pump will operate, or particular routines in order to activate and deactivate the suction pump in response to external stimuli. For example, it may be contemplated that a pressure sensor may be included within the pump housing element 36 or remote to the pump housing element 36 which may determine the pressure of a region within the sheath 12, and the control module 42 may be configured to actuate the pump element in response to the measured pressure rising above a predefined pressure. Alternatively, a pressure sensor, a blood pressure sensor, or a bloodflow sensor, or other type of sensor may be utilized to determine certain anatomical qualities indicative or related to of a wearer's level of sexual stimulation or qualities of a wearer's erection, and to actuate certain components within the pump housing element 36 in response to a determination thereof. For example, a pressure sensor could be utilized to determine that a wearer's penis is in the process of becoming erect, indicating the wearer is ready to commence engage in sexual intercourse, and could operate to trigger actuation of the suction pump in response thereto. Likewise, the same pressure sensor could detect when the wearer's penis has become sufficiently erect so as to exceed a certain predefined threshold as desired by the wearer, and may deactivate the suction pump in response to detection thereof. It may be appreciated that many such schemes are conceivable by one of ordinary skill in the art who has read and understood the preset disclosure, and thus are to be considered within the scope and spirit of the present disclosure.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An enhanced prophylactic device, the enhanced prophylactic device comprising:
    a sheath comprising an elastic tubular membrane having a closed distal end, an open proximal end, and an external side, the elastic tubular membrane having an air permeable region;
    a barrier positioned over an area of the external side of the elastic tubular membrane encompassing at least the air permeable region, the barrier and the area of the external side of the elastic tubular membrane over which the barrier is positioned defining a lumen region therebetween;
    a conduit defining an airflow pathway in fluid communication with the lumen region;
    a sealing element proximate to the open proximal end, the sealing element adapted to at least partially restrict the intrusion of ambient air into the open proximal end when the sheath is worn over a penis of a wearer; and
    a vacuum source comprising a suction pump, the suction pump being contained within a pump housing element;
    wherein when the sheath is worn over the penis of the wearer and the airflow pathway of the conduit is placed in fluid communication with the vacuum source, the enhanced prophylactic device is operative to reduce air pressure within the sheath to below ambient; and
    wherein the pump housing element is adapted to be worn by the wearer via annular engagement around a portion of the penis.

2. The enhanced prophylactic device of claim 1, wherein the suction pump is electronically powered.

3. The enhanced prophylactic device of claim 1, wherein the pump housing element is configured to be worn around a portion of the penis not enclosed by the sheath.

4. The enhanced prophylactic device of claim 1, wherein the pump housing element is configured to be worn around a portion of the penis at least partially enclosed by the sheath.

5. The enhanced prophylactic device of claim 4, wherein the pump housing element is configured to be worn over at least a portion of the sheath.

6. The enhanced prophylactic device of claim 4, wherein the pump housing element is configured to be worn underneath at least a portion of the sheath.

7. The enhanced prophylactic device of claim 1, wherein the pump housing element is integral with the sheath.

8. The enhanced prophylactic device of claim 1, wherein the pump housing element further comprises a stimulatory module adapted to intensify sexual stimulation of the wearer or a sexual partner of the wearer.

9. The enhanced prophylactic device of claim 8, wherein the stimulatory module comprises a vibrational element.

10. The enhanced prophylactic device of claim 1, wherein the pump housing element further comprises a power source for operating at least the suction pump.

11. The enhanced prophylactic device of claim 10, wherein the power source comprises a battery.

12. The enhanced prophylactic device of claim 1, wherein the pump housing element further comprises a control module for permitting the wearer to control the suction pump.

13. The enhanced prophylactic device of claim 12, wherein the control module comprises a toggle switch.

14. A method for treating sexual dysfunction, the method comprising the steps of:
  providing an enhanced prophylactic device, the enhanced prophylactic device comprising:
    a sheath comprising an elastic tubular membrane having a closed distal end, an open proximal end, and an external side, the elastic tubular membrane having an air permeable region;
    a barrier positioned over an area of the external side of the elastic tubular membrane encompassing at least the air permeable region, the barrier and the area of the external side of the elastic tubular membrane over which the barrier is positioned defining a lumen region therebetween;
    a conduit defining an airflow pathway in fluid communication with the lumen region;
    a sealing element proximate to the open proximal end, the sealing element adapted to at least partially restrict the intrusion of ambient air into the open proximal end when the sheath is worn over a penis of a wearer; and
    a vacuum source comprising a suction pump, the suction pump being contained within a pump housing element;
  positioning the sheath over the penis of the wearer;
  placing the airflow pathway of the conduit in fluid communication with the vacuum source so as to reduce air pressure within the sheath to below ambient; and
  annularly engaging the pump housing element around a portion of the penis of the wearer.

15. An enhanced prophylactic device, the enhanced prophylactic device comprising:
  a sheath comprising an elastic tubular membrane having a closed distal end, an open proximal end, and an external side, the elastic tubular membrane having an air permeable region;
  a barrier positioned over an area of the external side of the elastic tubular membrane encompassing at least the air permeable region, the barrier and the area of the external side of the elastic tubular membrane over which the barrier is positioned defining a lumen region therebetween;
  a conduit defining an airflow pathway in fluid communication with the lumen region;
  a sealing element proximate to the open proximal end, the sealing element adapted to at least partially restrict the intrusion of ambient air into the open proximal end when the sheath is worn over a penis of a wearer; and
  a vacuum source comprising a suction pump, the suction pump being contained within a pump housing element, the pump housing element being integral with the sealing element;
  wherein when the sheath is worn over the penis of the wearer and the airflow pathway of the conduit is placed in fluid communication with the vacuum source, the enhanced prophylactic device is operative to reduce air pressure within the sheath to below ambient.

* * * * *